United States Patent [19]

Foricher et al.

[11] Patent Number: 5,430,191
[45] Date of Patent: Jul. 4, 1995

[54] PHOSPHORUS COMPOUNDS

[75] Inventors: Joseph Foricher, Mulhouse, France; Rudolf Schmid, Arlesheim, Switzerland

[73] Assignee: Hoffmann-La Roche Inc., Nutley, N.J.

[21] Appl. No.: 122,506

[22] PCT Filed: Dec. 6, 1993

[86] PCT No.: PCT/CH93/00025
§ 371 Date: Sep. 27, 1993
§ 102(e) Date: Sep. 27, 1993

[87] PCT Pub. No.: WO93/15090
PCT Pub. Date: Aug. 5, 1993

[30] Foreign Application Priority Data

Jan. 31, 1992 [CH] Switzerland ............................ 289/92
Apr. 16, 1992 [CH] Switzerland ........................... 1270/92
May 18, 1992 [CH] Switzerland ........................... 1582/92
Jun. 19, 1992 [CH] Switzerland ........................... 1944/92

[51] Int. Cl.⁶ .............................................. C07F 9/50
[52] U.S. Cl. .......................................... 568/12; 568/13
[58] Field of Search .................................... 568/12, 13

[56] References Cited

U.S. PATENT DOCUMENTS 4,556,740 12/1985 Hansen et al. .......................... 568/13
5,021,593 6/1991 Nohira et al. ........................... 556/20

FOREIGN PATENT DOCUMENTS 104375 4/1984 European Pat. Off. .
398132 11/1990 European Pat. Off. .

OTHER PUBLICATIONS

Derwent Abstract B05 E11 J04 E19 (1990) for EP 398 132.

Greene et al., in "Protective Groups in Organic Synthesis, 2nd ed.", 1991, John Wiley & Sons, Inc., pp. 10–16.

Primary Examiner—Johann Richter
Assistant Examiner—Michael B. Hydorn
Attorney, Agent, or Firm—George M. Gould; George W. Johnston; Robert A. Silverman

[57] ABSTRACT

Novel racemic and optically active phosphorus compounds of the formula

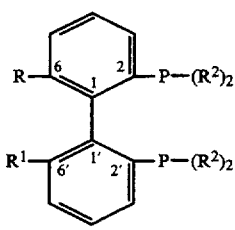

wherein R signifies hydroxy or a protected hydroxy group, $R^1$ represents hydroxy, a protected hydroxy group or lower alkoxy and $R^2$ represents lower alkyl, cycloalkyl, aryl or together with the phosphorus atom a group of the formula

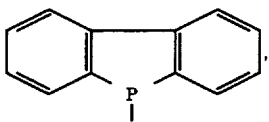

are described. The compounds of formula I are useful in the form of complexes with a metal of Group VIII as catalysts for asymmetric hydrogenations and for enantioselective hydrogen displacements in parochial, allylic systems.

10 Claims, No Drawings

PHOSPHORUS COMPOUNDS

This application is the National Stage Application of PCT/CH93/00025 filed Feb. 1, 1993.

The present invention is concerned with novel, racemic and optically active phosphorus compounds of the general formula

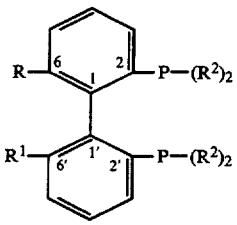
I wherein R signifies hydroxy or a protected hydroxy group, $R^1$ represents hydroxy, a protected hydroxy group or lower alkoxy and $R^2$ represents lower alkyl, cycloalkyl, aryl or together with the phosphorus atom a group of the formula

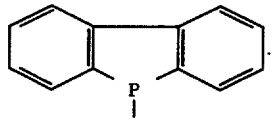

The invention is also concerned with the manufacture of the phosphorus compounds of formula I and with their use for enantioselective reactions such as e.g. asymmetric hydrogenations, enantioselective hydrogen displacements in prochiral, allylic systems, and the like. Moreover, the compounds of formula 1 in which R and $R^1$ both represent hydroxy groups can be used as starting materials for the manufacture of other diphosphines, e.g. of compounds of formula I in which R and/or $R^1$ represent(s) a protected hydroxy group.

The term "lower alkyl" signifies in the scope of the present invention straight-chain or branched alkyl groups with 1 to 5 carbon atoms such as methyl, ethyl, propyl, isopropyl, butyl, isobutyl, tert.butyl, pentyl, isopentyl and the like. The term "lower alkoxy" signifies groups in which the alkyl residue has the foregoing significance. As protecting groups for the hydroxy group there especially come into consideration in the scope of the present invention the usual ether-forming groups such as e.g. benzyl, allyl, benzyloxymethyl, lower alkoxymethyl or also 2-methoxyethoxymethyl and the like. The term "cycloalkyl" signifies here three- to seven-membered rings such as cyclopropyl, cyclobutyl, cyclopentyl, cyclohexyl and cycloheptyl, especially cyclopentyl and cyclohexyl. The term "aryl" signifies in the scope of the present invention especially the phenyl residue which can be not only unsubstituted but also multiply-substituted in the ortho-, meta- or para-position. Substituents which come into consideration in this case are phenyl, lower alkyl or lower alkoxy groups, preferably methyl or methoxy groups, or also di-lower alkyl-amino, preferably dimethylamino, groups, as well as fluorine or also trialkylsilyl such as trimethylsilyl and the like. Moreover, the term can also signify naphthyl.

The phosphorus compounds of formula I can be present not only in racemic form but also in optically active form. Preferred compounds of formula I are those in which R represents hydroxy and $R^1$ represents a protected hydroxy group or an alkoxy group, especially a benzyloxy group or an isopropyloxy group, and also those in which R and $R^1$ are the same, especially those in which R and $R^1$ both represent a hydroxy group or a benzyloxy group. Compounds in which $R^2$ represents phenyl, isopropyl, cyclopentyl or cyclohexyl are also preferred. Especially preferred compounds of formula I are:

(R)- or (S)-(6,6'-Dihydroxybiphenyl-2,2'-diyl)bis(diphenylphosphine), (R)- or (S)-(6,6'-dibenzyloxybiphenyl-2,2'-diyl)bis(diphenylphosphine ), (R)- or (S)-(6-hydroxy-6'-isopropoxybiphenyl-2,2'-diyl)bis(diphenylphosphine).

The compounds of formula I in accordance with the invention can be manufactured in a manner known per se. This can be carried out e.g. by subjecting a racemic or optically active compound of the general formula

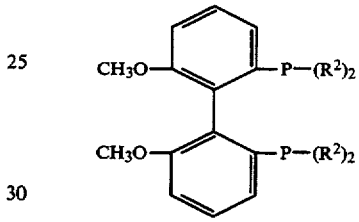
II wherein $R^2$ has the above significance, to an ether cleavage. There are thus obtained compounds of formula I in which R and $R^1$ signify hydroxy. Such compounds can, in turn, be readily converted in a manner known per se into compounds of formula I in which R and/or $R^1$ represent(s) a protected hydroxy group or into such compounds in which R signifies hydroxy and $R^1$ represents lower alkoxy.

The ether cleavage of a compound of formula I in which R represents lower alkoxy can be carried out in a manner known per se, e.g. by means of boron tribromide and the like. This is conveniently carried out in an inert organic solvent, e.g. in a halogenated hydrocarbon such as, for example, methylene chloride and the like, and at a temperature of about 30° to about −78° C.

The introduction of a hydroxy protecting group into a compound of formula I in which R and $R^1$ represent hydroxy can be carried out in a manner known per se, e.g. by reaction with a protecting group halide. e.g. benzyl chloride and the like. This reaction is conveniently carried out in an inert organic solvent in the presence of an inorganic base such as e.g. $K_2CO_3$, NaIl or KOH. As solvents there come into consideration e.g. acetone, N,N-dimethylformamide or in the case of KOH especially dimethyl sulphoxide. The reaction is also conveniently carried out at a temperature of about −10° C. to about 60° C., preferably at about 0° C. to about 25° C.

The conversion of a compound of formula I in which R and $R^1$ signify hydroxy into a compound of formula I in which $R^1$ represents lower alkoxy can also be carried out in a manner known per se, e.g. by monoalkylation. This is conveniently effected with a lower alkyl halide in an inert organic solvent in the presence of an inorganic base such as e.g. $K_2CO_3$, NaIl or KOH. As solvents there come into consideration e.g. acetone, N,N-dimethylformamide or in the case of KOH especially dimethyl sulphoxide. The reaction is also conveniently effected at a temperature of about −10° C. to about 60° C., preferably at about 0° to about 25° C.

The compounds of formula II which are used as starting materials are known compounds or analogues of known compounds which can be prepared readily in a manner analogous to the preparation of known compounds, for example according to Helv. Chim. Acta 74,370 (1991).

All of the previously mentioned reactions are conveniently carried out under an inert gas such as e.g. argon or nitrogen.

The phosphorus compounds of formula I in accordance with the invention form complexes with transition metals such as, for example, metals of Group VIII, especially with ruthenium, rhodium and iridium, which can be used as catalysts in asymmetric hydrogenations and also for enantioselective hydrogen displacements in prochiral, allylic systems. Ruthenium and rhodium complexes are preferred for the aforementioned hydrogenations, while rhodium complexes are preferred for isomerizations. These catalysts, i.e. the complexes from a metal of Group VIII and the phosphorus compounds of formula 1, are novel and are also an object of the present invention.

The aforementioned complexes can be manufactured in a manner known per se. e.g. by reacting a compound of formula I with a compound, which can yield a metal of Group VIII, in a suitable, inert organic or aqueous solvent. As suitable compounds which yield e.g. rhodium there can be mentioned, for example, organic rhodium complexes with ethylene, propylene and the like, as well as with bis-olefins, e.g. (Z,Z)-1,5-cyclooctadiene, 1,5hexadiene. bicyclo[2.2.1] hepta-2,5-diene, or with other dienes which form readily soluble complexes with rhodium. Preferred compounds which yield rhodium are e.g. di-μ-chloro-bis[η⁴-(Z,Z)-1,5-cyclooctadiene]dirhodium(I), di-η-chloro-bis[η⁴-norbornadiene]dirhodium(I), di-η-trifluoroacetato-bis[η⁴-(Z,Z)-1,5-cyclooctadiene]dirhodium(I), bis[η⁴-(Z,Z)-1,5-cyclooctadiene]rhodium tetrafluoroborate or bis[η⁴-(Z,Z)-cyclooctadiene]rhodium perchlorate. Di-μ-chloro-bis[η⁴-(Z,Z)- 1,5-cyclooctadiene]diiridium(I) can be mentioned, for example as a compound which yields iridium.

The aforementioned ruthenium complexes can be represented e.g. by the following formula

$Ru(Z)_2L$　　　III wherein Z represents halogen or the group A-COO, A represents lower alkyl, aryl, halogenated lower alkyl or halogenated aryl and L represents a chiral diphosphine ligand of formula 1.

These complexes can, in principle, be manufactured in a manner known per se. Conveniently and preferably, ruthenium complexes are manufactured, for example, by reacting a complex of the formula

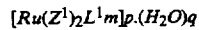
$[Ru(Z^1)_2L^1m]p.(H_2O)q$　　　IV wherein Z¹ represents halogen or a group A¹-COO, A¹ represents lower alkyl or halogenated lower alkyl, L¹ represents a neutral ligand, m represents the number 1, 2 or 3, p represents the number 1 or 2 and q represents the number 0 or 1;
with a chiral diphosphine ligand of formula I or by reacting a ruthenium complex of the formula

$Ru(CF_3COO)_2L$　　　V wherein L represents a chiral diphosphine ligand of formula I,
with a salt which yields the anion Z in which Z has the above significance.

The term "neutral ligand" signifies in the scope of the present invention a readily exchangeable ligand such as, for example, a diolefin, e.g. norbornadiene, (Z,Z)-1,5-cyclooctadiene etc., or a nitrile such as acetonitrile, benzonitrile and the like. Where m represents the number 2 or 3, the ligands can be the same or different.

The ruthenium complexes of formula IV are known substances of analogues of known substances which can be obtained readily in a manner analogous to the preparation of the known substances, for example according to Albers, M.O. et al., J. Organomet. Chem. 272. C62–C66 (1984).

The reaction of a ruthenium complex of formula IV with a chiral diphosphine ligand of formula I can be carried out in a manner known per se. This reaction can be conveniently carried out in an inert organic solvent. As examples of such solvents there can be mentioned e.g. ethers such as tetrahydrofuran or dioxan, ketones such as, for example, acetone, lower alcohols such as, for example, methanol, ethanol etc., halogenated hydrocarbons such as methylene chloride, chloroform and the like, or also mixtures of such solvents. Moreover, the reaction can be carried out at a temperature between about 0° C. and about 100° C., preferably between about 15° C. and about 60° C., but with the strict exclusion of oxygen.

The reaction of a ruthenium complex of formula V (obtainable from a complex of formula IV) with a salt which contains the anion Z can be carried out in a manner known per se. The term "a salt which yields the anion Z" signifies in the scope of the present invention, for example, ammonium salts, alkali metal salts or other suitable metal salts. In order to improve the solubility of such salts, crown ethers or the like can be added in certain instances.

As mentioned earlier, the phosphorus compounds in accordance with the invention in the form of complexes with metals of Group VIII, especially rhodium and ruthenium, can be used, inter alia, for asymmetric hydrogenations. As especially suitable substrates there can be mentioned in this connection particularly allyl alcohols such as e.g. geraniol, 6,7-dihydrogeraniol, 6,7-dihydrofarnesol, 6,7,10,11-tetrahydrofarnesol, (E)-3-(p-tert.-butylphenyl)-2-methyl-2-propen-2-ol and the like, enamides such as e.g. (Z)-2-acetyl-1 -(p-methoxybenzylidene)-1,2,3,4,5,6,7,8-octahydroisoquinoline as well as functionalized ketones such as β-ketoesters, e.g. methyl or ethyl acetoacetate etc., or also 2-pyridyl ketones such as e.g. 2-acetylpyridine, 2-pyridyl-2,8-bis(trifluormethyl)-4-quinolyl ketone and the like.

In carrying out such hydrogenations, these complexes can firstly be manufactured and then added to a solution of the substance to be hydrogenated. Alternatively, however, they can also be manufactured in situ, e.g. in the presence of a substance to be hydrogenated.

The asymmetric hydrogenation can be carried out in a suitable organic solvent which is inert under the reaction conditions. As such solvents there can be mentioned especially aromatic hydrocarbons such as benzene, toluene etc., lower alcohols such as e.g. methanol or ethanol, esters such as ethyl acetate, halogenated hydrocarbons such as methylene chloride, chloroform and the like, cyclic ethers such as tetrahydrofuran or dioxan, and the like, or mixtures of such solvents. Water or aqueous mixtures with organic solvents can also be used.

The ratio of metal to ligand L conveniently lies between about 0.05 and about 5 mol or between about 0.5 and about 2 mol, preferably at about 1 mol of metal per mol or ligand. The ratio of metal in the complexes such as e.g. of formula Ill to the substances to be hydrogenated conveniently lies between about 0.005 and about 1 mol %, preferably between about 0.002 and about 0.1 mol %.

The asymmetric hydrogenation with complexes such as e.g. of formula III is conveniently carried out at a temperature of about 0° C. to about 150° C. depending on the substrate which is used. This hydrogenation is also conveniently carried out under pressure, preferably at a pressure of about 2 to about 200 bar, particularly of about 10 to about 100 bar.

The phosphorus compounds of formula I in which R and/or $R^1$ represent(s) hydroxy are, in addition to their use mentioned earlier, also of interest in that they and the corresponding complexes with metals of Group VIII can be readily removed from reaction mixtures by adsorption on suitable ion exchangers.

The following Examples serve to illustrate the invention and do not in any manner represent a limitation. In these Examples the selected abbreviations have the following significances:

| TLC | thin layer chromatography |
| --- | --- |
| CC | capillary gas chromatograpy |
| e.e. | enantiomeric excess |
| RT | room temperature |

All temperatures are given in °Celsius.

EXAMPLE 1

Manufacture of (R)- or (S)-(6,6'-dihydroxybiphenyl-2,2'-diyl)bis(diphenylphosphine) [(R)- or (S)-HOBIPHEP]

A solution of 11.64 g (19.98 mmol) of (R)-(6,6'-dimethoxy-biphenyl-2,2'-diyl)bis(diphenylphosptnine) [=(R)-MeOBIPHEP)in 200 ml of $CH_2Cl_2$ (dried over molecular sieve) was cooled to $-78°$ C. under argon. A solution of 50 ml (50 mmol) of 1M $BBr_3$ in $CH_2Cl_2$ was then added slowly, with a white precipitate forming towards the end of the addition. The mixture was then warmed to room temperature and stirred for 24 hours. After hydrolysis with 400 ml of saturated $NH_4Cl$ for 1 hour, phase separation, drying of the organic phase ($CaCl_2$) and evaporation there were obtained 12.5 g of a yellow powder. After chromatography on silica gel (90 g, hexane/$CH_2Cl_2$ 1:1, hexane;ethyl acetat 9:1>3:2) there were obtained 8.26 g of (R)-HOBIPHEP as a white powder M.p. 198.2°–199.4°.$[\alpha]_D^{20}-34.7°$ (c=0.9, $CHCl_3$).

The reaction of 0.65 g (1.1 mmol) of (S)-MeOBIPHEP with 2.2 ml (2.2 mmol) of 1M $BBr_3$ in $CH_2Cl_2$ in a manner analogous to the foregoing gave 0.35 g of (S)-HOBIPHEP as a white powder, M.p. 199.5°–200.5°. $[\alpha]_D^{20}=+33.9°$ (c=1, $CHCl_3$).

EXAMPLE 2

0.5g (0.90 mmol) of (R)-(6,6'-dihydroxybiphenyl-2,2'-diyl)bis(diphenylphosphine) [prepared according to Example 1] was added under argon to a suspension of 0.216 g (7.20 mmol) of NaH in 10 ml of dimethylformamide. The mixture was stirred at RT for 30 minutes, with hydrogen evolution being observed. Then, 0.83 ml (7.20 mmol) of benzyl chloride was added and the reaction mixture was stirred at RT for 3 hours. By hydrolysis with saturated $NH_4Cl$ solution and extraction with ether there were obtained 1.07 g of a yellow-orange oil. Chromatography on silica gel (20 g, hexane/ethyl acetate 4:1) and subsequent filtration of a hexane solution on about 5 g of silica gel gave 0.58 g of a white powder. By addition of about 10 ml of ethanol, separation of insoluble material by filtration on about 10 g of silica gel and subsequent crystallization from toluene/ethanol there were obtained 410 mg of (R)-(6,6'-dibenzyloxybiphenyl2,2'-diyl)bis(diphenylphosphine) [(R)-BnOBIPHEP] as white crystals. M.p. 171.5–171.6°; $[\alpha]_D^{20}=17.1°$(c=1, $CHCl_3$).

EXAMPLE 3

A solution of 2.0 g (3.61 mmol) of (R)-(6,6'-dihydroxy-biphenyl-2,2'-diyl)bis(diphenylphosphine) [prepared a Example 1] in 40 ml of dimethyl sulphoxide was stirred at RT under argon for 30 minutes with 0.572 g (10.19 mmol) of powdered 80% KOH. Then. 1.13 ml (12.03 mmol) of isopropyl bromide were added dropwise and the mixture was stirred at RT for a further 23 hours. By hydrolysis with 30 ml of saturated NH4Cl solution, extraction with about 175 ml of ether, drying of the organic phase ($Na_2SO_4$) and evaporation there were obtained 2.41 g of a white powder. After chromatography on 70 g of silica gel (hexane/CHCl2) there were obtained 1.18 g of (R)-(6,6'-diisopropyloxybiphenyl-2,2'-diyl)bis(diphenylphosphine) as a white solid. Further elution then gave 0.45 g of (R)-(6-hydroxy6'-isopropyloxybiphenyl-2,2'-diyl)bis(diphenylphosphine) [(R)IpropO/HOBIPHEP] as white solid M.p. 76.1–77°; $[\alpha]_D^{20}=-46.0°$(c=1, $CHCl_3$).

EXAMPLE 4 a) A suspension of 0.375 g (0.43 mmol) of [Ru(CF3COO)2(COD)]2 in 16 ml of diethyl ether/tetrahydrofuran (1:1) was stirred at 40° overnight with 0.466 g (0.84 mmol) of (R)-HO-BIPHEP (prepared according to Example 1). After removing the solvent the residue was dried in a vacuum and the solid residue was washed twice with 10 ml of pentane each time while stirring. After drying in a vacuum there was obtained 0.72 g of [Ru(CF3COO)2((R)-HOBIPHEP)].

A suspension of 3.0 g (3.40 mmol) of [Ru(CF3COO)2((R)-HOBIPHEP)] in 30 ml of methanol was treated with 1.0 g (12.0 mmol) of sodium acetate and stirred at 45° for 2 hours. After removing the solvent the residue was dried in a vacuum and subsequently added to a frit The product was extracted with 60 ml of methylene chloride, the solvent was then removed and the residue was triturated with 30 ml of pentane. The supernatant solution was pipetted off and the residual powder was dried in a vacuum. 2.5 g of Ru(CH3COO)2[(R)-HOBIPHEP] were obtained.

b) A 500 ml autoclave was loaded in a glove box with 15.0 g (50.4 mmol) of (Z)-2-acetyl-1-(p-methoxybenzylidene)-1,2,3,4,5,6,7,8-octahydroisoquinoline, 170 ml of methanol and 3.9 mg (0.0050 mmol) of Ru(CH3COO)2[(R)-HOBIPHEP] as the catalyst. The hydrogenation was carried out at 100° and 35 bar for 22 hours. The conversion was 98.5%. A 2 g product-containing aliquot of the hydrogenation solution was evaporated and the residue was dissolved in diethyl ether. The ether solution was filtered through a silica gel pad in order to separate the catalyst. Evaporation of the filtrate gave 1.97 g of (S)-2-acetyl-1-(p-methoxybenzyl)-1,2,3.4,5,6,7,8-octahydroisoquinoline as yellowish crystals of 95.9% e.e.

In order to determine the e.e, value, the product was hydrolyzed at 170° for 18 hours in a mixture of ethylene glycol and 40° aqueous potassium hydroxide solution. The amine formed was converted with (−)-camphanoyl chloride in pyridine/4dimethylaminopyridine to the mixture of diastereomeric amides and the latter was analyzed by GC.

EXAMPLE 5

A catalyst solution was prepared in a 50 ml of measuring flask in a glove box ($O_2$ content <1 ppm) by dissolving 9.7 mg (0.02 mmol) of dichloro-bis-(1,5-cyclooctadiene)dirhodium and 21.9 mg (0.04 mMol) (R)-HOBIPHEP in 50 ml of toluene. 5 ml of this catalyst solution were added to a solution of 16.1 g (78.85 mmol) of (E)-3-(p-tert.butylphenyl)-2-methyl-2-propen1-ol [(E)-dehydroliliol] in 145 ml of toluene in a 500 ml autoclave. The hydrogenation was carried out at 100°, a constant pressure of 60 bar and while stirring intensively. The conversion was 99.9% after 21 hours. The pale yellow hydrogenation solution was rinsed from the autoclave and evaporated at 60°/17 mbar on a rotary evaporator. The residue was distilled at 140°/0.01 mbar. There were obtained 16.1 g (99.0%) of (S) -3-(p-tert.butylphenyl)-2-methyl-1-propanol [(S)-liliol], as a colourless oil with an enantiomeric purity of 96.2% e.e.

In order to determine the e.e. value, the product in methylene chloride was converted with (R)- or (S)-6-methoxy-2,5,7,8 -tetramethylchromane-2-carboxylic acid, dicyclohexylcarbodiimide and 4-dimethylaminopyridine into the diastereomeric ester and analyzed by gas chromatography. EXAMPLE 6

A catalyst solution having (R)-IpropO/HOBIPHEP as the ligand was prepared in an analogous manner to Example 5 and the hydrogenation was carried out under the same conditions. The conversion was 99.9% after 21 hours. The hydrogenation solution was worked up as in Example 5. There were obtained 16.1 g (99.0%) of (S)-liliol as a colourless oil with an enantiomeric purity of 95.1% e.e

We claim:

1. Racemic and optically active phosphorous compounds of the formula

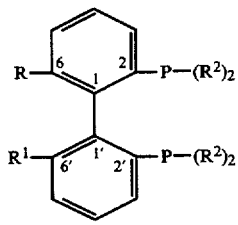

wherein R is hydroxy or a protected hydroxy group wherein the protecting group is selected from the group consisting of benzyl, allyl, benzyloxymethyl, lower alkoxymethyl and 2-methoxyethoxymethyl, $R^1$ is hydroxy, a protected hydroxy group or lower alkoxy wherein the protecting group is selected from the group consisting of benzyl, allyl, benzyloxymethyl, lower alkoxymethyl and 2-methoxyethoxymethyl; and $R^2$ is lower alkyl, cycloalkyl, aryl or together with the phosphorous atom a group of the formula

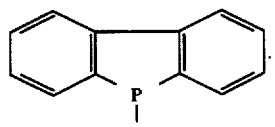

2. Racemic and optically active phosphorus compounds of formula I according to claim 1, wherein R and $R^1$ are the same.

3. Racemic and optically active phosphorus compounds of formula I according to claim 1, wherein R represents hydroxy and $R^1$ represents a protected hydroxy group.

4. Racemic and optically active phosphorus compounds of formula I according to claim 1 wherein R and $R^1$ represent hydroxy or a benzyloxy group.

5. Racemic and optically active phosphorus compounds of formula I according to claim 1 wherein R represents hydroxy and $R^1$ represents a benzyloxy group or an isopropyloxy group.

6. A compound of formula I according to claim 1, the compound being (R)- or (S)-(6,6'-Dihydroxybiphenyl-2,2,'-diyl)bis(diphenylphosphine).

7. A compound of formula I according to claim 1, the compound being (R)- or (S)-(6,6'-Dibenzyloxybiphenyl-2,2,'-diyl)bis(diphenylphosphine).

8. A compound of formula I according to claim the compound being (R)- or (S)-(6-Hydroxy-6'-isopropoxybiphenyl -2,2 '-diyl) bis (diphenylphosphine) .

9. Racemic and optically active phosphorous compounds of formula I according to claim 2 wherein R and $R^1$ represent hydroxy or a benzyloxy group.

10. Racemic and optically active compounds of formula I according to claim 3 wherein R represents hydroxy and $R^1$ represents a benzyloxy group or an isopropyloxy group.

* * * * *

UNITED STATES PATENT AND TRADEMARK OFFICE
CERTIFICATE OF CORRECTION

PATENT NO. : 5,430,191
DATED : July 4, 1995
INVENTOR(S) : Joseph Foricher, Rudolf Schmid It is certified that error appears in the above-indentified patent and that said Letters Patent is hereby corrected as shown below:

On the title page item [22], "PCT Filed: Dec. 6, 1993"

should read --- PCT Filed: Feb. 1, 1993 --- .

Claim 8, Column 8, line 49: "to claim the" should read --- to claim 1, the --- .

Signed and Sealed this

Nineteenth Day of September, 1995

Attest:

BRUCE LEHMAN

*Attesting Officer*     *Commissioner of Patents and Trademarks*